(12) United States Patent
Matsumoto

(10) Patent No.: US 9,597,270 B2
(45) Date of Patent: *Mar. 21, 2017

(54) HYDROGEL-FORMING MATERIAL

(71) Applicant: NISSAN CHEMICAL INDUSTRIES, LTD., Tokyo (JP)

(72) Inventor: Keigo Matsumoto, Funabashi (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/433,171

(22) PCT Filed: Oct. 2, 2013

(86) PCT No.: PCT/JP2013/076837
§ 371 (c)(1),
(2) Date: Apr. 2, 2015

(87) PCT Pub. No.: WO2014/054699
PCT Pub. Date: Apr. 10, 2014

(65) Prior Publication Data
US 2015/0250692 A1    Sep. 10, 2015

(30) Foreign Application Priority Data

Oct. 3, 2012 (JP) ................................. 2012-221632

(51) Int. Cl.
| | | |
|---|---|---|
| A61K 47/00 | (2006.01) | |
| A23L 1/05 | (2006.01) | |
| A61K 8/36 | (2006.01) | |
| A61K 47/12 | (2006.01) | |
| A61K 47/18 | (2006.01) | |
| A61K 9/06 | (2006.01) | |
| A61K 47/42 | (2006.01) | |
| A61K 8/04 | (2006.01) | |
| A61K 8/64 | (2006.01) | |
| A61Q 19/00 | (2006.01) | |

(52) U.S. Cl.
CPC .............. *A61K 8/361* (2013.01); *A23L 29/20* (2016.08); *A61K 8/042* (2013.01); *A61K 8/64* (2013.01); *A61K 9/06* (2013.01); *A61K 47/12* (2013.01); *A61K 47/183* (2013.01); *A61K 47/42* (2013.01); *A61Q 19/00* (2013.01); *A23V 2002/00* (2013.01); *A23V 2250/55* (2013.01); *A61K 2800/10* (2013.01)

(58) Field of Classification Search
CPC ............ A23V 2250/55; A23V 2002/00; A61K 2800/10; A61K 47/12; A61K 47/183; A61K 8/042; A61K 8/361; A61K 8/64; A61K 9/06; A61K 47/42; A61Q 19/00; A23L 1/05
USPC .............. 514/773; 524/17; 426/573
See application file for complete search history.

(56) References Cited

U.S. PATENT DOCUMENTS

| | | | | |
|---|---|---|---|---|
| 8,486,896 B2 * | 7/2013 | Miyachi | .................... | A23L 1/05 |
| | | | | 252/182.12 |
| 8,716,248 B2 * | 5/2014 | Miyachi | .................... | A23L 1/05 |
| | | | | 252/182.12 |

(Continued)

FOREIGN PATENT DOCUMENTS

| | | |
|---|---|---|
| CN | 102596164 A | 7/2012 |
| CN | 104582826 A | 4/2015 |

(Continued)

OTHER PUBLICATIONS

Hamachi et al., "Solid Phase Lipid Synthesis (SPLS) for Construction of an Artificial Glycolipid Library," Chem. Commun., 2000, pp. 1281-1282.
Suzuki et al., "Supramolecular Hydrogels Formed by L-Lysine Derivatives," Chemistry Letters, 2004, vol. 33, No. 11, pp. 1496-1497.
Jung et al., "Self-Assembly of a Sugar-Based Gelator in Water: Its Remarkable Diversity in Gelation Ability and Aggregate Structure," Langmuir, vol. 17, 2001, pp. 7299-7232.
Hamachi et al., "Solid-Phase Lipid Synthesis (SPLS)-2: Incidental Discovery of Organogelators Based on Artificial Glycolipids," Tetrahedron Letters, 2001, vol. 42, pp. 6141-6145.

(Continued)

*Primary Examiner* — My-Chau T Tran
(74) *Attorney, Agent, or Firm* — Oliff PLC

(57) ABSTRACT

A hydrogel-forming material for preparing hydrogel even after a process of stirring gelator in medium heat to dissolve and disperse the gelator, and cooling the mixture to room temperature with stirring, a hydrogel material wherein a gel can reform by standing at room temperature even after a hydrogel obtained using the material is converted sol by shaking. The hydrogel-forming material with lipid peptide gelator includes Formula (1) or a pharmaceutically usable salt thereof:

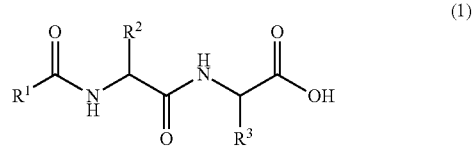

(1)

$R^1$ is a $C_{9-23}$ aliphatic group, $R^2$ is a hydrogen atom or $C_{1-4}$ alkyl group optionally having a $C_{1-2}$ branched chain, $R^3$ is a —$(CH_2)_n$—X group, n is 1 to 4, and X is an amino-group, guanidino group, $CONH_2$ group, 5-membered ring optionally having 1-3 nitrogen atom(s), 6-membered ring optionally having 1-3 nitrogen atom(s), or fused heterocycle composed of 5-membered ring and 6-membered rings optionally having 1-3 nitrogen atom(s), water, and fatty acid salt as additive.

5 Claims, No Drawings

(56) References Cited

U.S. PATENT DOCUMENTS

| | | | | |
|---|---|---|---|---|
| 8,816,049 B2* | 8/2014 | Miyachi | ............... | C07K 5/1008 |
| | | | | 530/330 |
| 8,916,682 B2* | 12/2014 | Miyachi | ............... | C07K 5/1008 |
| | | | | 530/330 |
| 8,999,300 B2* | 4/2015 | Iwama | ..................... | A61K 8/64 |
| | | | | 424/195.18 |
| 9,265,833 B2* | 2/2016 | Miyamoto | ............ | A61K 9/0014 |
| 9,289,496 B2* | 3/2016 | Miyamoto | ............ | A61K 9/0014 |
| 9,328,137 B2* | 5/2016 | Matsumoto | ......... | C07K 5/06026 |
| 9,333,158 B2* | 5/2016 | Miyamoto | ............. | A61K 8/046 |
| 2012/0035108 A1 | 2/2012 | Miyamoto et al. | | |
| 2012/0258059 A1 | 10/2012 | Iwama et al. | | |
| 2013/0084305 A1* | 4/2013 | Iwama | ..................... | A61K 8/64 |
| | | | | 424/195.18 |
| 2014/0113976 A1* | 4/2014 | Matsumoto | .............. | A61K 8/64 |
| | | | | 514/773 |
| 2015/0202586 A1* | 7/2015 | Imoto | ..................... | A61K 8/64 |
| | | | | 516/103 |
| 2015/0250880 A1* | 9/2015 | Matsumoto | .............. | A61K 8/64 |
| | | | | 524/17 |
| 2016/0129119 A1* | 5/2016 | Imoto | ................ | C07K 5/06026 |
| | | | | 514/773 |

FOREIGN PATENT DOCUMENTS

| | | |
|---|---|---|
| JP | H08-53693 A | 2/1996 |
| WO | 2009/005151 A1 | 1/2009 |
| WO | 2009/005152 A1 | 1/2009 |
| WO | 2010/106981 A1 | 9/2010 |
| WO | 2011/052613 A1 | 5/2011 |
| WO | 2012/063947 A1 | 5/2012 |
| WO | 2012/133787 A1 | 10/2012 |
| WO | 2012/144609 A1 | 10/2012 |

OTHER PUBLICATIONS

Suzuki et al., "Supramoledular Hydrogel Formed by Glucoheptonamide of L-Lysine: Simple Preparation and Excellent Hydrogelation Ability," Tetrahedron, 2007, vol. 63, pp. 7302-7308.

Matsuzawa et al., "Assembly and Photoinduced Organization of Mono- and Oligopeptide Molecules Containing an Azobenzene Moiety," Adv. Funct. Mater., 2007, vol. 17, No. 9, pp. 1507-1514.

Jan. 7, 2014 International Search Report issued in International Application No. PCT/JP2013/076837.

Jan. 7, 2014 Written Opinion issued in International Application No. PCT/JP2013/076837.

Nov. 30, 2016 Office Action issued in Chinese Patent Application No. 201380059210.1.

\* cited by examiner

HYDROGEL-FORMING MATERIAL

TECHNICAL FIELD

The present invention relates to a hydrogel-forming material having a low molecular weight lipid peptide compound, and in particular, to a hydrogel-forming material in which a hydrogel forming operation is easy and a gel can be reformed, and a hydrogel obtained from the same.

BACKGROUND ART

Since a hydrogel contains water as a medium, it is useful as a gel having high biocompatibility and is used in various fields including applications for commodities such as a paper diaper, cosmetics, and fragrances.

Examples of a conventional hydrogel may include a polymer gel formed by cross-linking a polymer chain to form a three-dimensional net structure, and forming a non-covalent bond between the structure and a medium such as water to swell the structure. For a natural polymer gel formed from a polysaccharide such as an agarose or a protein, and a synthetic polymer gel in which polymer chains are cross-linked through a chemical covalent bond, such as an acrylamide gel, many researches of physical properties and application developments of the polymer gel have been carried out.

In recent years, in addition to the gels formed from the polymers described above, a hydrogel formed by self-assembly of an organic compound having relatively low molecular weight has been found, and widely studied.

Most of the low molecular weight gelators that have been proposed are amphipathic compounds having a long chain alkyl group as a hydrophobic moiety in combination with a hydrophilic moiety. Examples thereof may include an amphipathic compound in which the hydrophilic moiety is amino acid (Non-Patent Document 1), an amphipathic compound in which the hydrophilic moiety is peptide (Patent Documents 1 and 2), an amphipathic compound in which the hydrophilic moiety is saccharide (Non-Patent Documents 2 and 3), and an amphipathic compound in which the hydrophilic moiety is polyol (Non-Patent Document 4). In addition, a low molecular weight gelator utilizing a property in which a peptide consisting of valine easily forms a β-sheet structure is also proposed (Non-Patent Document 5).

Using such a low molecular weight hydrogelator, a hydrogel can be formed by stirring the hydrogelator and water as a medium with heating under a temperature condition of about 100° C., dissolving and dispersing the gelator in water, and then allowing the solution to stand at room temperature.

PRIOR ART DOCUMENTS

Patent Documents

Patent Document 1: WO 2009/005151 Pamphlet
Patent Document 2: WO 2009/005152 Pamphlet

Non-Patent Documents

Non-Patent Document 1: Suzuki, Masahiro., Yumoto, Mariko., Mutsumi, Shirai., Hirofusa, Hanabusa, Kenji., Chemistry Letters, 33(11), 1496-1497.
Non-Patent Document 2: Jong Hwa Jung, Georeg John, Mitsutosish Mausda, Kaname Yoshida, Seiji Shinnkai, and Toshimi Shimizu Langumir, 2001, 17, 7229-7232

Non-Patent Document 3: I. Hamachi, S. Kiyonaka, S. Shinkai, Tetrahedron Lett., 2001, 42, 6141.
I. Hamachi, S. Kiyonaka, S. Shinaki, Chem. Commun., 2000, 1281.
Non-Patent Document 4: Masahiro Suzuki, Sanae Owa, Hirofusa Shirai and Kenji Hanabusa, Tetrahedron 2007, 63, 7302-7308.
Non-Patent Document 5: Yoko Matsuzawa, Katsuyuki Ueki, Masaru Yoshida, Nobuyuki Tamaoki, Tohru Nakamura, Hideki Sakai, and Masahiko Abe, Adv. Funct. Mater., 2007, 17, 1507-1514

SUMMARY OF THE INVENTION

Problem to be Solved by the Invention

However, in order to form a gel using the low molecular weight gelator that has been disclosed at least by the applicant, it is necessary to carry out a process of stirring the gelator in the medium with heating to dissolve and disperse the gelator, and then allowing the system to stand at room temperature until the system is cooled. Since this process prevents the system to be uniformly cooled with scale up, the quality of hydrogel obtained is likely to be non-uniform in the system. Therefore, this process results in a production condition which is disadvantageous in terms of operability and quality control during production of a hydrogel in an industrial scale. That is, improvements in productivity and consistency in quality have been required when a hydrogel is produced in a large scale.

In most of the gel-forming materials that have been proposed, a gel cannot be reformed after a formed hydrogel is converted into a sol by shaking. In materials allowing repeated use of a hydrogel, differences in gel usability after multiple uses has been a problem. That is, improvements in performance in repeated use of a hydrogel have been required.

The present invention is based on such circumstances, and the problem to be solved by the present invention is to provide a hydrogel-forming material in which a hydrogel can be formed in preparation of the hydrogel even after a process of stirring a gelator in a medium with heating to dissolve and disperse the gelator, and cooling the mixture to room temperature with stirring, and a hydrogel material in which a gel can be reformed by standing at room temperature even after a hydrogel obtained using the material is converted into a sol by shaking.

Means for Solving the Problem

In order to solve the problem, the present inventors have intensively studied, and as a result, found that when a specific fatty acid salt is added as an additive in formation of a hydrogel from a lipid peptide gelator containing a low molecular weight peptide or a pharmaceutically usable salt thereof and water, a hydrogel can be formed even after a process of dispersing with heating, followed by cooling with stirring, and a gel can be reformed by standing at room temperature even after the obtained hydrogel is converted into a sol by shaking. Thus, the present invention has been accomplished.

Specifically, as a first aspect, the present invention relates to a hydrogel-forming material comprising a lipid peptide gelator consisting of at least one of a compound of the following Formula (1) or a pharmaceutically usable salt of the compound:

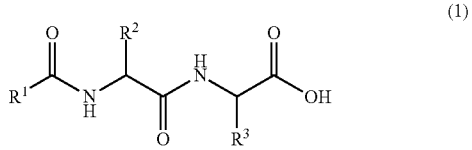

(wherein, $R^1$ is a $C_{9-23}$ aliphatic group, $R^2$ is a hydrogen atom or a $C_{1-4}$ alkyl group optionally having a $C_{1-2}$ branched chain, $R^3$ is a —$(CH_2)_n$—X group, n is a number of 1 to 4, and X is an amino group, a guanidino group, a —$CONH_2$ group, a 5-membered ring optionally having 1 to 3 nitrogen atom(s), a 6-membered ring optionally having 1 to 3 nitrogen atom(s), or a fused heterocycle composed of a 5-membered ring and a 6-membered ring optionally having 1 to 3 nitrogen atom(s).), water, and a fatty acid salt as an additive.

As a second aspect, the present invention relates to the hydrogel-forming material according to the first aspect, in which the additive is at least one fatty acid salt selected from the group consisting of butyrate, valerate, caproate, enanthate, caprylate, pelargonate, caprate, laurate, myristate, pentadecylate, palmitate, palmitoleate, margarate, stearate, oleate, vaccenate, linoleate, (9,12,15)-linolenate, (6,9,12)-linolenate, eleostearate, tuberculostearate, arachidate, arachidonate, behenate, lignocerate, nervonate, cerotate, montanate, and melissate.

As a third aspect, the present invention relates to a hydrogel formed using the hydrogel-forming material according to the first or second aspect.

As a fourth aspect, the present invention relates to the hydrogel according to the third aspect having a pH of 8 to 11.

Effects of the Invention

The hydrogel-forming material of the present invention contains a specific fatty acid salt as the additive, and therefore a good hydrogel can be easily obtained without formation of an insoluble substance or a deposited substance even after stirring and cooling during formation of a gel using the hydrogel-forming material. That is, the present invention can provide a hydrogel-forming material of which both operability and consistency in quality are improved in production of a hydrogel in an industrial scale.

In the hydrogel-forming material of the present invention, even when a hydrogel formed once is shaken to be converted into a sol state, and then is allowed to stand at room temperature, a gel can be formed again. That is, the present invention can provide a hydrogel-forming material of which the performance of a hydrogel after repeated use is also improved.

The lipid peptide gelator contained in the hydrogel-forming material of the present invention is a highly safe artificial low molecular weight compound composed of only lipid and peptide, and the fatty acid salt contained as the additive is an additive generally used for foods, cosmetics, or pharmaceuticals. That is, the hydrogel-forming material of the present invention provides excellent biological safety, and in particular, is extremely useful for applications of a medium for cell culture, a medical material, a material for cosmetics, and the like, from the viewpoint of high safety required for such applications.

The hydrogel-forming material of the present invention is a material that can form a hydrogel by causing water to gel without a cross-linker or the like that is required for formation of the synthetic polymer gel which has been conventionally proposed, for example. Thus, in the obtained hydrogel, there occurs no problem such as remaining of unreacted material such as unreacted cross-linker. Further, the hydrogel-forming material can form a hydrogel even when the amount of the gelator to be added is as small as about 100 mM, and the hydrogel-forming material has low impact on the environment and the organism when it is incorporated thereto.

In addition, the hydrogel of the present invention can be obtained by adding the gelator in a smaller amount compared with the conventional proposal as described above, and therefore it can be said that the hydrogel is a hydrogel having high safety in terms of the organism and the environment.

As described above, a hydrogel obtained from a lipid peptide as a low molecular weight compound has low impact on the environment and the organism. This is because the hydrogel is easily decomposed by soil bacteria and the like for use in the external environment, for example, in soil, and because it can be easily decomposed by metabolic enzymes for use in the organism.

MODES FOR CARRYING OUT THE INVENTION

The present invention relates to a hydrogel-forming material comprising a lipid peptide gelator consisting of at least one of a compound of Formula (1) or a pharmaceutically usable salt thereof, which are described below in detail, water, and a specific fatty acid salt as an additive.

Hereinafter, each component will be described.

[Lipid Peptide Gelator]

As the lipid peptide gelator used in the present invention, a compound (lipid peptide) of the following Formula (1) or a pharmaceutically usable salt thereof (low molecular weight compound having a lipid moiety as a hydrophobic moiety and a peptide moiety as a hydrophilic moiety) can be used.

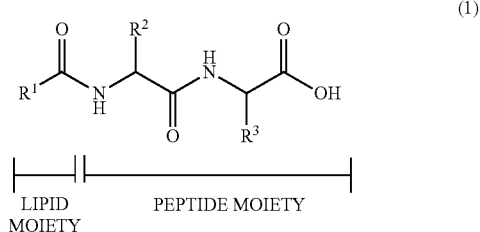

In Formula (1), it is desirable that $R^1$ be a $C_{9-23}$ aliphatic group, and preferably a linear $C_{11-23}$ aliphatic group optionally having 0 to 2 unsaturated bonds.

Specific examples of a lipid moiety (acyl group) including $R^1$ and an adjacent carbonyl group may include a lauroyl group, a dodecylcarbonyl group, a myristoyl group, a tetradecylcarbonyl group, a palmitoyl group, a margaroyl group, an oleoyl group, an elaidoyl group, a linoleyl group, a stearoyl group, a vaccenoyl group, a octadecylcarbonyl group, an arachidoyl group, an eicosylcarbonyl group, a behenoyl group, an alkanoyl group, a docosylcarbonyl group, a lignoceyl group, and a nervonoyl group. A lauroyl group, a myristoyl group, a palmitoyl group, a margaroyl group, a stearoyl group, an oleoyl group, an elaidoyl group, and a behenoyl group are particularly preferred.

In Formula (1), $R^2$ in the peptide moiety is a hydrogen atom or a $C_{1-4}$ alkyl group optionally having a $C_{1-2}$ branched chain.

The $C_{1-4}$ alkyl group optionally having a $C_{1-2}$ branched chain means an alkyl group that has a $C_{1-4}$ main chain and may have a $C_{1-2}$ branched chain. Specific examples thereof may include a methyl group, an ethyl group, a n-propyl group, an i-propyl group, an n-butyl group, an i-butyl group, a sec-butyl group, and a tert-butyl group.

$R^2$ is preferably a hydrogen atom or a $C_{1-3}$ alkyl group optionally having a $C_1$ branched chain, and more preferably a hydrogen atom.

The $C_{1-3}$ alkyl group optionally having a $C_1$ branched chain means an alkyl group that has a $C_{1-3}$ main chain and may have a $C_1$ branched chain. Specific examples thereof may include a methyl group, an ethyl group, a n-propyl group, an i-propyl group, an i-butyl group, and a sec-butyl group. A methyl group, an i-propyl group, an i-butyl group, and a sec-butyl group are preferred.

In Formula (1), $R^3$ is a $-(CH_2)_n-X$ group. In the $-(CH_2)_n-X$ group, n is a number of 1 to 4, and X is an amino group, a guanidino group, a $-CONH_2$ group, a 5-membered ring optionally having 1 to 3 nitrogen atom(s), a 6-membered ring optionally having 1 to 3 nitrogen atom(s), or a fused heterocycle composed of a 5-membered ring and a 6-membered ring optionally having 1 to 3 nitrogen atom(s).

In the $-(CH_2)_n-X$ group of $R^3$, X is preferably an amino group, a guanidino group, a carbamoyl group ($-CONH_2$ group), a pyrrole group, an imidazole group, a pyrazole group, or an indole group, and more preferably an imidazole group. In the $-(CH_2)_n-X$ group, n is preferably 1 or 2, and more preferably 1.

Therefore, the $-(CH_2)_n-$ group is preferably an aminomethyl group, a 2-aminoethyl group, a 3-aminopropyl group, a 4-aminobutyl group, a carbamoylmethyl group, a 2-carbamoylethyl group, a 3-carbamoylbutyl group, a 2-guanidinoethyl group, a 3-guanidinobutyl group, a pyrrolemethyl group, a 4-imidazolemethyl group, a pyrazolemethyl group, or a 3-indolemethyl group, more preferably a 4-aminobutyl group, a carbamoylmethyl group, a 2-carbamoylethyl group, a 3-guanidinobutyl group, a 4-imidazolemethyl group, or a 3-indolemethyl group, and further preferably a 4-imidazolemethyl group.

Among the compounds of Formula (1), a lipid peptide that is particularly suitable as a lipid peptide gelator is a compound having a lipid moiety and a peptide moiety (amino acid assembly) shown below (abbreviations of amino acids are alanine (Ala), asparagine (Asn), glutamine (Gln), glycine (Gly), histidine (His), isoleucine (Ile), leucine (Leu), lysine (Lys), tryptophan (Trp), and valine (Val)): lauroyl-Gly-His, lauroyl-Gly-Gln, lauroyl-Gly-Asn, lauroyl-Gly-Trp, lauroyl-Gly-Lys, lauroyl-Ala-His, lauroyl-Ala-Gln, lauroyl-Ala-Asn, lauroyl-Ala-Trp, lauroyl-Ala-Lys; myristoyl-Gly-His, myristoyl-Gly-Gln, myristoyl-Gly-Asn, myristoyl-Gly-Trp, myristoyl-Gly-Lys, myristoyl-Ala-His, myristoyl-Ala-Gln, myristoyl-Ala-Asn, myristoyl-Ala-Trp, myristoyl-Ala-Lys; palmitoyl-Gly-His, palmitoyl-Gly-Gln, palmitoyl-Gly-Asn, palmitoyl-Gly-Trp, palmitoyl-Gly-Lys, palmitoyl-Ala-His, palmitoyl-Ala-Gln, palmitoyl-Ala-Asn, palmitoyl-Ala-Trp, palmitoyl-Ala-Lys; stearoyl-Gly-His, stearoyl-Gly-Gln, stearoyl-Gly-Asn, stearoyl-Gly-Trp, stearoyl-Gly-Lys, stearoyl-Ala-His, stearoyl-Ala-Gln, stearoyl-Ala-Asn, stearoyl-Ala-Trp, stearoyl-Ala-Lys.

Lauroyl-Gly-His, lauroyl-Ala-His, myristoyl-Gly-His, myristoyl-Ala-His, palmitoyl-Gly-His, palmitoyl-Ala-His, stearoyl-Gly-His, and stearoyl-Ala-His are mentioned as most preferred.

In the hydrogel-forming material of the present invention, the ratio of the lipid peptide gelator to be blended is for example, 0.1 to 200 mM (mol/m$^3$), preferably 0.5 to 100 mM, and more preferably 1 to 50 mM relative to the total volume of the hydrogel-forming material.

The lipid peptide gelator used in the present invention consists of at least one of the compound (lipid peptide) of Formula (1) or a pharmaceutically usable salt thereof, and as the hydrogelator, these compounds may be used singly or in combination of two or more of them.

[Additive]

As an additive used for the hydrogel-forming material of the present invention, a fatty acid salt that is an additive generally used for foods, cosmetics, or pharmaceuticals can be used.

The additive used for the hydrogel-forming material of the present invention is not particularly limited as long as it is the above-mentioned fatty acid salt. Examples thereof may include butyrate, valerate, caproate, enanthate, caprylate, pelargonate, caprate, laurate, myristate, pentadecylate, palmitate, palmitoleate, margarate, stearate, oleate, vaccenate, linoleate, (9,12,15)-linolenate, (6,9,12)-linolenate, eleostearate, tuberculostearate, arachidate, arachidonate, behenate, lignocerate, nervonate, cerotate, montanate, and melissate. Among these, laurate, myristate, palmitate, stearate, and oleate are preferred.

These additives may be used in a form of fatty acid salt singly or in a form of mixed acid salt of two or more of them.

Examples of the organic acid salt may include a sodium salt or a potassium salt, and a sodium salt is particularly preferred.

In the hydrogel-forming material of the present invention, the ratio of the additive to be blended is for example, 0.1 to 200 mM, preferably 0.5 to 100 mM, and more preferably 1 to 50 mM relative to the total volume of the hydrogel-forming material.

The fatty acid salt is at least one selected from the fatty acid salt group described above, and these fatty acid salt(s) may be used singly or in combination of two or more of them.

[Hydrogel-Forming Material]

The gel-forming material of the present invention comprises a lipid peptide gelator consisting of at least one of the compound of Formula (1) or a pharmaceutically usable salt thereof, water, and an additive.

In the gel-forming material, the components described above are blended, and heated under a temperature condition of about 100° C., preferably with stirring, to easily dissolve and disperse the lipid peptide gelator in water as a medium.

In this case, the time of heating with stirring varies depending on the type of lipid peptide gelator or additive used, or the blending amount thereof, and is usually about 20 minutes to about 90 minutes.

Thus, the gel forming-material in a solution form in which the lipid peptide gelator is being dissolved and dispersed is cooled at room temperature (about 25° C.) and allowed to stand to obtain a hydrogel. In the gel forming-material of the present invention, the gel forming-material in a solution form in which the lipid peptide gelator is being dissolved and dispersed after heating is cooled with stirring using a stir bar to a temperature lower than the heating temperature, for example, room temperature to 80° C., or room temperature to about 40° C., and then allowed to cool and stand at room temperature (about 25° C.) to obtain a hydrogel.

[Hydrogel]

A subject of the present invention is also a hydrogel formed using the hydrogel-forming material described above.

The obtained hydrogel is preferably a gel having a pH of 8 to 11.

[Hydrogel-Forming Mechanism]

The gel-forming material of the present invention, particularly the low molecular weight compound of Formula (1) (lipid peptide), is added to water, and dissolved and dispersed, and as a result, the peptide moiety in Formula (1) forms an intermolecular non-covalent bond through a hydrogen bond, while the lipid moiety in Formula (1) is hydrophobically packed for self-assembly (also called self-organization) so as to form a fiber. The shape of the fiber is not limited, and examples thereof may include a cylindrical shape and a plate shape.

When the fiber is formed in water, the fiber forms a three-dimensional network structure and a non-covalent bond between the hydrophilic moiety (peptide moiety) on the fiber surface and an aqueous medium, so that the fiber swells. Thus, the whole aqueous solution is caused to gel to form a hydrogel.

As described above, the hydrogel-forming material of the present invention (and the gel obtained from the same) is a material having excellent biological safety since the low molecular weight gelator including a naturally derived raw material such as fatty acid and amino acid is used as a gelator, and an organic acid or a salt thereof generally used as an additive for foods, cosmetics, or pharmaceuticals is used.

In the hydrogel-forming material of the present invention, a hydrogel can be formed by dissolving and dispersing the gelator and the like in the medium contained in the material under heating, and allowing the mixture to stand at room temperature as it is (without stirring). In addition, a hydrogel can be formed by allowing the mixture to stand at room temperature, even after cooling it with stirring.

Further, a gel can be reformed by shaking the obtained hydrogel to convert it into a sol, and allowing the sol to stand again at room temperature.

As described above, the hydrogel-forming material of the present invention is a material which is extremely useful in actual use such as production of a hydrogel in an industrial scale that frequently causes an issue of consistent quality (uniformity) or repeated use. The hydrogel-forming material can be used for materials in various fields such as a medium for cell culture, a preservation material for a biomolecule such as a cell and a protein, a base material for external use, a medical material, a material for biochemistry, a material for cosmetics, a material for foods, a contact lens, a paper diaper, an artificial actuator, and a material for dry-land agriculture.

EXAMPLES

Hereinafter, the present invention will be described in detail with reference to Examples and Test Examples, but the present invention is not limited to the Examples.

Synthesis Example 1

Synthesis of Lipid Peptide (N-palmitoyl-Gly-His)

In this Example, a lipid peptide used as a gelator was synthesized by the following method.

14.2 g (91.6 mmol) of histidine, 30.0 g (91.6 mmol) of N-palmitoyl-Gly-methyl, and 300 g of toluene were placed in a 500-mL 4-necked flask, and 35.3 g (183.2 mmol) of sodium methoxide 28% methanol solution was added as a base. The mixture was heated in an oil bath at 60° C. and stirred over 1 hour. The oil bath was then removed, and the solution was allowed to cool to 25° C., followed by reprecipitation with 600 g of acetone and filtration. The resultant solid was dissolved in a mixed solution of 600 g of water and 750 g of methanol. To the solution, 30.5 mL (183.2 mmol) of 6N hydrochloric acid was added for neutralization to precipitate a solid, and the solution was filtered. Subsequently, the obtained solid was dissolved in a mixed solution of 120 g of tetrahydrofuran and 30 g of water at 60° C., and 150 g of ethyl acetate was added. The mixture was cooled from 60° C. to 30° C. The precipitated solid was then collected by filtration. The collected solid was dissolved in a solvent of 120 g of tetrahydrofuran and 60 g of acetonitrile. The mixture was heated to 60° C., stirred for 1 hour, cooled, and filtered. The obtained solid was washed with 120 g of water, followed by filtration. The solid was dried under reduced pressure to obtain 26.9 g (yield 65%) of free form of N-palmitoyl-Gly-His (hereinafter also simply referred to as N-palmitoyl-Gly-His) as a white crystal.

Examples 1 to 7 and Comparative Example 1

Evaluation Test of Hydrogelation Ability of N-palmitoyl-Gly-His for Each Additive N-palmitoyl-Gly-His prepared in the Synthesis Example was added so that the concentration of N-palmitoyl-Gly-His was 20 mM and the concentration of each fatty acid sodium (Na) salt was 20 to 1 mM (solvent: ultrapure water) (in Comparative Example 1, a fatty acid sodium salt was not added) in a Mighty vial (No. 3, manufactured by Maruemu corporation). The mixture was heated at 100° C. for 60 minutes with dry bath Sahara320 (manufactured by AS ONE Corporation), and it was visually confirmed whether or not dispersion occurred. In evaluation of dispersibility, a case where a solid content was not seen was determined as ○, and a case where a solid content was not completely dissolved and a residue remained was determined as x, from the appearance after heating.

Then, the mixture was allowed to cool at room temperature overnight. In evaluation of hydrogelation ability, a state where the solution had no flowability and did not run off even when the vial was placed in reverse was determined as "gelation (○)," and a state where the solution run off was determined as "no gelation (x)." The presence or absence of syneresis in the gel was confirmed, and if the mixture was caused to gel, the pH of the gel was measured with Twin pH meter (manufactured by AS ONE Corporation). A final composition after a hydrogelation test and obtained test results are shown in the following tables. In the tables, "-" indicates that the test is not performed.

Example 1

Sodium Caproate

TABLE 1

| Composition | Concentration (mM) | | |
|---|---|---|---|
| N-palmitoyl-Gly-His | 20 | 20 | 20 |
| Sodium caproate | 1 | 5 | 20 |

TABLE 1-continued

| Composition | Concentration (mM) | | |
|---|---|---|---|
| Test results are as follows | | | |
| Heating time | 60 minutes | 60 minutes | 60 minutes |
| Evaluation of dispersibility | ○ | ○ | ○ |
| Evaluation of hydrogelation ability | ○ | X | X |
| Syneresis | None | — | — |
| pH | 8.8 | — | — |

Example 2

Sodium Caprylate

TABLE 2

| Composition | Concentration (mM) | | |
|---|---|---|---|
| N-palmitoyl-Gly-His | 20 | 20 | 20 |
| Sodium caprylate | 1 | 5 | 20 |
| Test results are as follows | | | |
| Heating time | 60 minutes | 60 minutes | 60 minutes |
| Evaluation of dispersibility | ○ | ○ | ○ |
| Evaluation of hydrogelation ability | ○ | ○ | ○ |
| Syneresis | None | None | None |
| pH | 8.7 | 8.3 | 8.1 |

Example 3

Sodium Laurate

TABLE 3

| Composition | Concentration (mM) | | |
|---|---|---|---|
| N-palmitoyl-Gly-His | 20 | 20 | 20 |
| Sodium laurate | 1 | 5 | 20 |
| Test results are as follows | | | |
| Heating time | 60 minutes | 60 minutes | 60 minutes |
| Evaluation of dispersibility | ○ | ○ | ○ |
| Evaluation of hydrogelation ability | ○ | ○ | ○ |
| Syneresis | None | None | None |
| pH | 8.9 | 9.2 | 9.4 |

Example 4

Sodium Myristate

TABLE 4

| Composition | Concentration (mM) | | |
|---|---|---|---|
| N-palmitoyl-Gly-His | 20 | 20 | 20 |
| Sodium myristate | 1 | 5 | 20 |
| Test results are as follows | | | |
| Heating time | 60 minutes | 60 minutes | 60 minutes |
| Evaluation of dispersibility | ○ | ○ | ○ |

TABLE 4-continued

| Composition | Concentration (mM) | | |
|---|---|---|---|
| Evaluation of hydrogelation ability | ○ | ○ | ○ |
| Syneresis | None | None | None |
| pH | 9.4 | 9.8 | 9.9 |

Example 5

Sodium Palmitate

TABLE 5

| Composition | Concentration (mM) | | |
|---|---|---|---|
| N-palmitoyl-Gly-His | 20 | 20 | 20 |
| Sodium palmitate | 1 | 5 | 20 |
| Test results are as follows | | | |
| Heating time | 60 minutes | 60 minutes | 60 minutes |
| Evaluation of dispersibility | ○ | ○ | ○ |
| Evaluation of hydrogelation ability | ○ | ○ | ○ |
| Syneresis | None | None | None |
| pH | 9.6 | 10.1 | 10.5 |

Example 6

Sodium Stearate

TABLE 6

| Composition | Concentration (mM) | | |
|---|---|---|---|
| N-palmitoyl-Gly-His | 20 | 20 | 20 |
| Sodium stearate | 1 | 5 | 20 |
| Test results are as follows | | | |
| Heating time | 60 minutes | 60 minutes | 60 minutes |
| Evaluation of dispersibility | ○ | ○ | ○ |
| Evaluation of hydrogelation ability | ○ | ○ | ○ |
| Syneresis | None | None | None |
| pH | 9.4 | 9.6 | 10.3 |

Example 7

Sodium Oleate

TABLE 7

| Composition | Concentration (mM) | | |
|---|---|---|---|
| N-palmitoyl-Gly-His | 20 | 20 | 20 |
| Sodium oleate | 1 | 5 | 20 |
| Test results are as follows | | | |
| Heating time | 60 minutes | 60 minutes | 60 minutes |
| Evaluation of dispersibility | ○ | ○ | ○ |
| Evaluation of hydrogelation ability | ○ | X | ○ |
| Syneresis | None | — | Present |
| pH | 9.2 | 9.6 | 9.5 |

Comparative Example 1

Without Fatty Acid Sodium

TABLE 8

| Composition | Concentration (mM) |
|---|---|
| N-palmitoyl-Gly-His | 20 |
| Test results are as follows | |
| Heating time | 60 minutes |
| Evaluation of dispersibility | ○ |
| Evaluation of hydrogelation ability | ○ |
| Syneresis | None |
| pH | 8.7 |

Examples 8 to 9 and Comparative Example 2

Evaluation Test of Hydrogelation Ability after Cooling with Stirring of N-palmitoyl-Gly-His for Each Additive N-palmitoyl-Gly-His prepared in the Synthesis Example was added so that the concentration of N-palmitoyl-Gly-His was 20 mM and the concentration of each fatty acid sodium (Na) salt was 20 to 1 mM (solvent: ultrapure water) (in Comparative Example 2, a fatty acid sodium salt was not added) in a Mighty vial (No. 3, manufactured by Maruemu corporation). The mixture was heated at 100° C. for 60 minutes with dry bath Sahara320 (manufactured by AS ONE Corporation), and it was visually confirmed whether or not dispersion occurred. In evaluation of dispersibility, a case where a solid content was not seen was determined as ○, and a case where a solid content was not completely dissolved and a residue remained was determined as x, from the appearance after heating.

Subsequently, a stir bar (3 mm×15 mm, manufactured by AS ONE Corporation) was placed into the vial, and the mixture was allowed to cool with stirring for 30 minutes by multistirrer M3 (manufactured by AS ONE Corporation).

Then, the mixture was allowed to cool at room temperature overnight. In evaluation of hydrogelation ability, a state where the solution had no flowability and did not run off even when the vial was placed in reverse was determined as "gelation (○)," and a state where the solution run off was determined as "no gelation (x)." The presence or absence of syncresis in the gel was confirmed, and if the mixture was caused to gel, the pH of the gel was measured with Twin pH meter (manufactured by AS ONE Corporation). A final composition after a hydrogelation test and obtained test results are shown in the following tables. In the tables, "-" indicates that the test is not performed.

As shown in the following tables, in Examples 8 and 9 in which sodium myristate and sodium palmitate were added respectively, hydrogelation ability was confirmed even after cooling with stirring. However, in Comparative Example 2 in which a fatty acid sodium salt was not added, a hydrogel was not formed even after cooling with stirring.

Example 8

Sodium Myristate

TABLE 9

| Composition | Concentration (mM) | | |
|---|---|---|---|
| N-palmitoyl-Gly-His | 20 | 20 | 20 |
| Sodium myristate | 1 | 5 | 20 |
| Test results are as follows | | | |
| Heating time | 60 minutes | 60 minutes | 60 minutes |
| Evaluation of dispersibility | ○ | ○ | ○ |
| Evaluation of hydrogelation ability after cooling with stirring | X | ○ | ○ |
| Syneresis | — | None | None |
| pH | — | 10 | 10.2 |

Example 9

Sodium Palmitate

TABLE 10

| Composition | Concentration (mM) | | |
|---|---|---|---|
| N-palmitoyl-Gly-His | 20 | 20 | 20 |
| Sodium palmitate | 1 | 5 | 20 |
| Test results are as follows | | | |
| Heating time | 60 minutes | 60 minutes | 60 minutes |
| Evaluation of dispersibility | ○ | ○ | ○ |
| Evaluation of hydrogelation ability after cooling with stirring | X | ○ | ○ |
| Syneresis | — | None | None |
| pH | — | 10 | 10.3 |

Comparative Example 2

Without Fatty Acid Sodium

TABLE 11

| Composition | Concentration (mM) |
|---|---|
| N-palmitoyl-Gly-His | 20 |
| Test results are as follows | |
| Heating time | 60 minutes |
| Evaluation of dispersibility | ○ |
| Evaluation of hydrogelation ability after cooling with stirring | X |
| Syneresis | — |
| pH | 8.7 |

Examples 10 to 14 and Comparative Example 3

Evaluation Test of Reformation of N-palmitoyl-Gly-His for Each Additive

N-palmitoyl-Gly-His prepared in the Synthesis Example was added so that the concentration of N-palmitoyl-Gly-His was 20 mM and the concentration of each fatty acid sodium (Na) salt was 20 to 1 mM (solvent: ultrapure water) (in Comparative Example 3, a fatty acid sodium salt was not added) in a Mighty vial (No. 3, manufactured by Maruemu corporation). The mixture was heated at 100° C. for 60 minutes with dry bath Sahara320 (manufactured by AS ONE Corporation), and it was visually confirmed whether or not dispersion occurred. In evaluation of dispersibility, a case where a solid content was not seen was determined as ○, and a case where a solid content was not completely dissolved and a residue remained was determined as x, from the appearance after heating.

Then, the mixture was allowed to cool at room temperature overnight. In evaluation of hydrogelation ability, a state where the solution had no flowability and did not run off even when the vial was placed in reverse was determined as "gelation (○)," and a state where the solution run off was determined as "no gelation (x)."

The mixture caused to gel was stirred with a vortex mixer (manufactured by Scientific Industries Inc.) to be converted into a sol. After then, the sol was allowed to stand at room temperature overnight. In evaluation of reformation ability of a hydrogel, a state where the solution had no flowability and did not run off even when the vial was placed in reverse was determined as "reformation (○)," and a state where the solution run off was determined as "no reformation (x)."

The presence or absence of syneresis in the reformed gel was confirmed, and if the gel was reformed, the pH of the gel was measured with Twin pH meter (manufactured by AS ONE Corporation). A final composition after a hydrogelation test and obtained test results are shown in the following tables. In the tables, "-" indicates that the test is not performed.

As shown in the following tables, in Examples 10 to 14 in which each fatty acid sodium salt was added, reformation ability of the hydrogel was confirmed. However, in Comparative Example 3 in which a fatty acid sodium salt was not added, a hydrogel was not reformed after conversion into a sol.

Example 10

Sodium Laurate

TABLE 12

| Composition | Concentration (mM) | | |
|---|---|---|---|
| N-palmitoyl-Gly-His | 20 | 20 | 20 |
| Sodium laurate | 1 | 5 | 20 |
| Test results are as follows | | | |
| Heating time | 60 minutes | 60 minutes | 60 minutes |
| Evaluation of dispersibility | ○ | ○ | ○ |
| Evaluation of hydrogelation ability | ○ | ○ | ○ |
| Evaluation of hydrogel reformation ability | X | ○ | ○ |
| Syneresis | — | None | None |
| pH | — | 9.0 | 9.5 |

Example 11

Sodium Myristate

TABLE 13

| Composition | Concentration (mM) | | |
|---|---|---|---|
| N-palmitoyl-Gly-His | 20 | 20 | 20 |
| Sodium myristate | 1 | 5 | 20 |
| Test results are as follows | | | |
| Heating time | 60 minutes | 60 minutes | 60 minutes |
| Evaluation of dispersibility | ○ | ○ | ○ |
| Evaluation of hydrogelation ability | ○ | ○ | ○ |
| Evaluation of hydrogel reformation ability | X | ○ | ○ |
| Syneresis | — | None | None |
| pH | — | 9.9 | 9.9 |

Example 12

Sodium Palmitate

TABLE 14

| Composition | Concentration (mM) | | |
|---|---|---|---|
| N-palmitoyl-Gly-His | 20 | 20 | 20 |
| Sodium palmitate | 1 | 5 | 20 |
| Test results are as follows | | | |
| Heating time | 60 minutes | 60 minutes | 60 minutes |
| Evaluation of dispersibility | ○ | ○ | ○ |
| Evaluation of hydrogelation ability | ○ | ○ | ○ |
| Evaluation of hydrogel reformation ability | X | X | ○ |
| Syneresis | — | — | None |
| pH | — | — | 10.1 |

Example 13

Sodium Stearate

TABLE 15

| Composition | Concentration (mM) | | |
|---|---|---|---|
| N-palmitoyl-Gly-His | 20 | 20 | 20 |
| Sodium stearate | 1 | 5 | 20 |
| Test results are as follows | | | |
| Heating time | 60 minutes | 60 minutes | 60 minutes |
| Evaluation of dispersibility | ○ | ○ | ○ |
| Evaluation of hydrogelation ability | ○ | ○ | ○ |
| Evaluation of hydrogel reformation ability | X | ○ | ○ |
| Syneresis | — | None | None |
| pH | — | 9.7 | 10.1 |

Example 14

Sodium Oleate

TABLE 16

| Composition | Concentration (mM) | | |
|---|---|---|---|
| N-palmitoyl-Gly-His | 20 | 20 | 20 |
| Sodium oleate | 1 | 5 | 20 |
| Test results are as follows | | | |
| Heating time | 60 minutes | 60 minutes | 60 minutes |
| Evaluation of dispersibility | ○ | ○ | ○ |
| Evaluation of hydrogelation ability | ○ | ○ | ○ |
| Evaluation of hydrogel reformation ability | X | ○ | X |
| Syneresis | — | None | — |
| pH | — | 9.7 | — |

Comparative Example 3

Without Fatty Acid Sodium

TABLE 17

| Composition | Concentration (mM) |
|---|---|
| N-palmitoyl-Gly-His | 20 |
| Test results are as follows | |
| Heating time | 60 minutes |
| Evaluation of dispersibility | ○ |
| Evaluation of hydrogelation ability | ○ |
| Evaluation of hydrogel reformation ability | X |
| Syneresis | — |
| pH | 8.7 |

The invention claimed is:

1. A hydrogel-forming material comprising water, a fatty acid salt as an additive, and a lipid peptide gelator consisting of at least one of a compound of Formula (1) or a pharmaceutically usable salt of the compound:

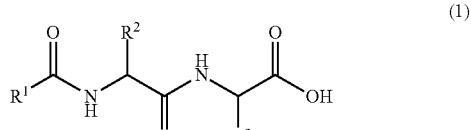

(1)

wherein, $R^1$ is a $C_{9-23}$ aliphatic group, $R^2$ is a hydrogen atom or a $C_{1-4}$ alkyl group optionally having a $C_{1-2}$ branched chain, $R^3$ is a —$(CH_2)_n$—X group, n is a number of 1 to 4, and X is an amino group, a guanidino group, a —$CONH_2$ group, a 5-membered ring optionally having 1 to 3 nitrogen atom(s), a 6-membered ring optionally having 1 to 3 nitrogen atom(s), or a fused heterocycle composed of a 5-membered ring and a 6-membered ring optionally having 1 to 3 nitrogen atom(s).

2. The hydrogel-forming material according to claim 1, wherein the additive is at least one fatty acid salt selected from the group consisting of butyrate, valerate, caproate, enanthate, caprylate, pelargonate, caprate, laurate, myristate, pentadecylate, palmitate, palmitoleate, margarate, stearate, oleate, vaccenate, linoleate, (9,12,15)-linolenate, (6,9,12)-linolenate, eleostearate, tuberculostearate, arachidate, arachidonate, behenate, lignocerate, nervonate, cerotate, montanate, and melissate.

3. A hydrogel formed using the hydrogel-forming material according to claim 1.

4. The hydrogel according to claim 3 having a pH of 8 to 11.

5. A hydrogel formed using the hydrogel-forming material according to claim 2.

* * * * *